US00PP34742P2

(12) United States Plant Patent
Lazzeri

(10) Patent No.: US PP34,742 P2
(45) Date of Patent: Nov. 15, 2022

(54) ***PELARGONIUM* PLANT NAMED 'LVPI1801'**

(50) Latin Name: ***Pelargonium peltatum* X *Pelargonium zonale***
Varietal Denomination: LVPI1801

(71) Applicant: Carlo Lazzeri, Vacaria (BR)

(72) Inventor: Carlo Lazzeri, Vacaria (BR)

( * ) Notice: Subject to any disclaimer, the term of this patent is extended or adjusted under 35 U.S.C. 154(b) by 0 days.

(21) Appl. No.: 17/732,416

(22) Filed: Apr. 28, 2022

Related U.S. Application Data

(60) Provisional application No. 63/182,282, filed on Apr. 30, 2021.

(51) Int. Cl.
*A01H 5/02* (2018.01)
*A01H 6/42* (2018.01)

(52) U.S. Cl.
USPC ..... Plt./324

(58) Field of Classification Search
USPC ..... Plt./324, 325, 326, 332
CPC ... A01H 5/02; A01H 5/00; A01H 6/42; A01H 6/425; A01H 6/00
See application file for complete search history.

(56) References Cited

PUBLICATIONS

Dummen Orange Interspecific Geranium, retrieved on May 27, 2022 at https://siteadmin.dummenorange.com/site/documents/7797/santana.pdf, 3 pp. (Year: 2022).*

* cited by examiner

*Primary Examiner* — June Hwu
(74) *Attorney, Agent, or Firm* — C. Anne Whealy

(57) ABSTRACT

A new and distinct interspecific *Pelargonium* plant named 'LVPI1801', characterized by its compact and upright to broadly spreading plant habit; moderately vigorous to vigorous growth habit; freely branching habit; durable dark green-colored leaves; freely and early flowering habit; single white-colored flowers with purplish pink-colored basal spots that are held above the foliar plane on moderately strong peduncles; and good garden performance.

2 Drawing Sheets

Figure 1:
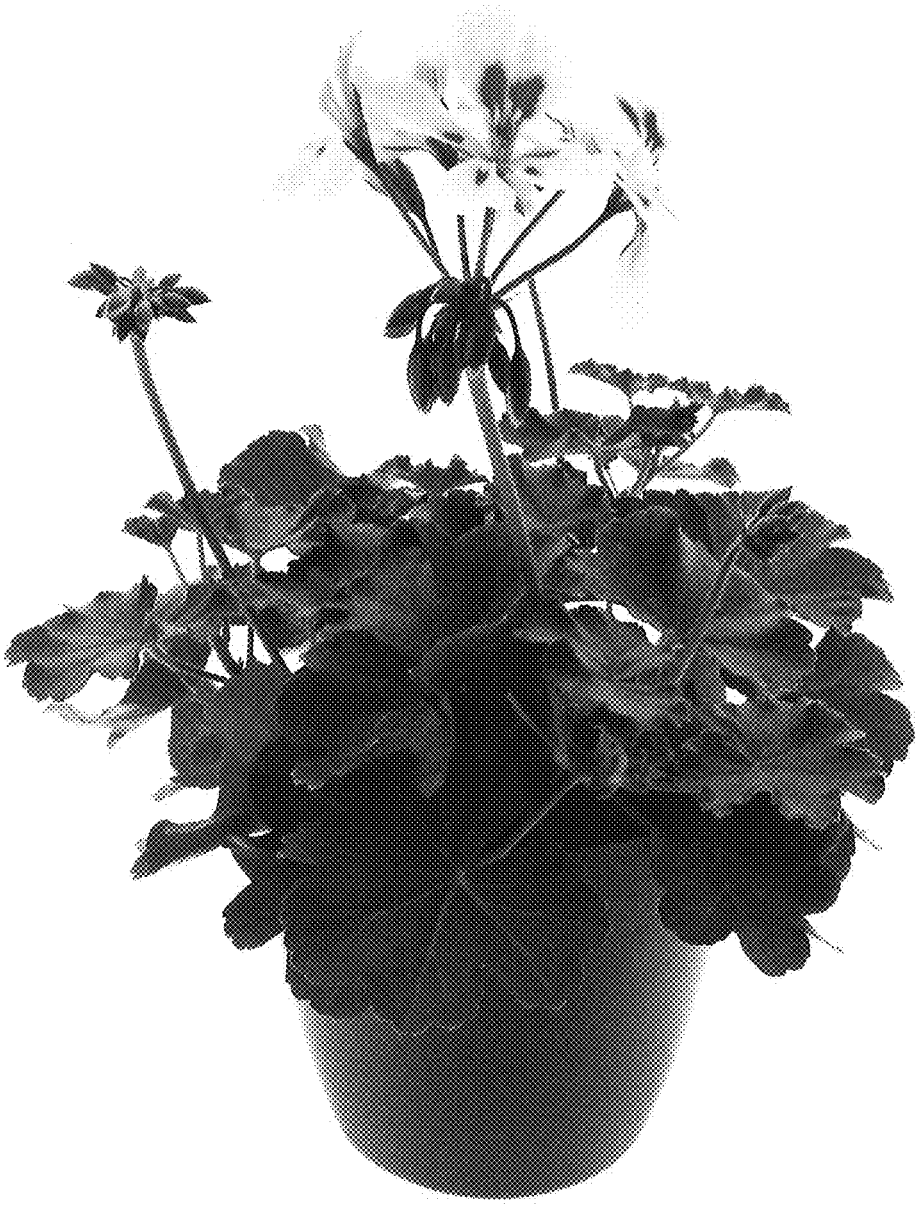

Botanical designation: *Pelargonium peltatum* X *Pelargonium zonale.*
Cultivar denomination: 'LVPI1801'.

CROSS-REFERENCED TO CLOSELY-RELATED APPLICATIONS

Title: Varieties of *Pelargonium* Plants
Inventor/Applicant: Carlo Lazzeri
Filed: Apr. 30, 2021
Ser. No.: 63/182,282
Inventor/Applicant hereby claims the benefit of this provisional U.S. Patent Application.

STATEMENT REGARDING PRIOR DISCLOSURES BY INVENTOR/APPLICANT

An European Plant Breeders' Rights application for the instant plant was filed by the Inventor/Applicant on Apr. 20, 2021, application number 2021/1076. Foreign priority is not claimed to this application.

The Inventor/Applicant assert that no publications nor advertisements relating to sales, offers for sale or public distribution occurred more than one year prior to the effective filing date of this application. Any information about the claimed plant would have been obtained from a direct or indirect disclosure from the Inventor/Applicant. Inventor/Applicant claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of interspecific *Pelargonium* plant, botanically known as *Pelargonium peltatum* X *Pelargonium zonale*, and hereinafter referred to by the name 'LVPI1801'.

The new interspecific *Pelargonium* plant is a product of a planned breeding program conducted by the Inventor in Vacaria, Brazil. The objective of the breeding program is to develop new strong and freely flowering interspecific *Pelargonium* plants with attractive flowers and good garden performance.

The new interspecific *Pelargonium* plant originated from a cross-pollination in January, 2017 in Vacaria, Brazil of *Pelargonium peltatum* 'Figradol Pink', trade name, Grand Idols Pink, disclosed in U.S. Plant Pat. No. 20,562, as the female, or seed, parent with *Pelargonium zonale* 'Gran Gala Dark with Magenta Eye', not patented, as the male, or pollen, parent. The new interspecific *Pelargonium* plant was discovered and selected by the Inventor as a single flowering plant from within the progeny of the stated cross-pollination grown in a controlled greenhouse environment in Vacaria, Brazil in January, 2018.

Asexual reproduction of the new interspecific *Pelargonium* plant by terminal stem cuttings in a controlled environment in Vacaria, Brazil since April, 2018 has shown that the unique features of this new interspecific *Pelargonium* plant are stable and reproduced true to type in successive generations.

SUMMARY OF THE INVENTION

Plants of the new interspecific *Pelargonium* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'LVPI1801'. These characteristics in combination distinguish 'LVPI1801' as a new and distinct interspecific *Pelargonium* plant:

1. Compact and upright to broadly spreading plant habit.
2. Moderately vigorous to vigorous growth habit.
3. Freely branching habit.
4. Durable dark green-colored leaves.
5. Freely and early flowering habit.
6. Single white-colored flowers with purplish pink-colored basal spots that are held above the foliar plane on moderately strong peduncles.
7. Good garden performance.

Plants of the new interspecific *Pelargonium* can be compared to plants of female parent, 'Figradol Pink'. In side-by-side comparisons, plants of the new interspecific *Pelargonium* differ primarily from plants of 'Figradol Pink' in the following characteristics:

1. Plants of the new interspecific *Pelargonium* are more upright than and not as trailing as plants of 'Figradol Pink'.
2. Leaf margins of plants of the new interspecific *Pelargonium* have shallower sinuses than leaf margins of plants of 'Figradol Pink'.
3. Flowers of plants of the new interspecific *Pelargonium* are white in color with purplish pink-colored basal spots whereas flowers of plants of 'Figradol Pink' are pink in color with red purple-colored venation.

Plants of the new interspecific *Pelargonium* can be compared to plants of male parent, 'Gran Gala Dark with Magenta Eye'. In side-by-side comparisons, plants of the new interspecific *Pelargonium* differ primarily from plants of 'Gran Gala Dark with Magenta Eye' in the following characteristics:

1. Plants of the new interspecific *Pelargonium* are more broadly spreading than and not as upright as plants of 'Gran Gala Dark with Magenta Eye'.
2. Plants of the new interspecific *Pelargonium* have smaller flowers than plants of 'Gran Gala Dark with Magenta Eye'.

Plants of the new interspecific *Pelargonium* can be compared to plants of the interspecific *Pelargonium*, 'Caldera Red', not patented. In side-by-side comparisons, plants of the new interspecific *Pelargonium* differ primarily from plants of 'Caldera Red' in the following characteristics:

1. Plants of the new interspecific *Pelargonium* are more vigorous than plants of 'Caldera Red'.
2. Plants of the new interspecific *Pelargonium* have larger leaves than plants of 'Caldera Red'.
3. Plants of the new interspecific *Pelargonium* have larger flowers than plants of 'Caldera Red'.

BRIEF DESCRIPTION OF THE PHOTOGRAPHS

The accompanying colored photographs illustrate the overall appearance of the new interspecific *Pelargonium* plant showing the colors as true as it is reasonably possible to obtain in colored reproductions of this type. Colors in the photographs may differ slightly from the color values cited in the detailed botanical description which accurately describe the colors of the new interspecific *Pelargonium* plant.

The photograph on the first sheet (FIG. 1) is a side perspective view of a typical flowering plant of 'LVPI1801' grown in a container.

Figure 2:
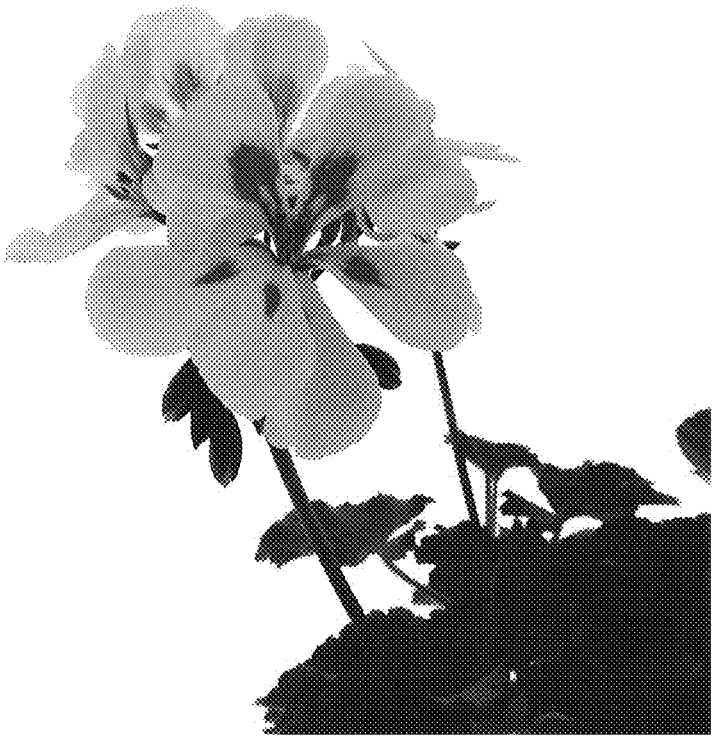

The photograph at the top of the second sheet (FIG. 2) is a close-up view of a typical flowering plant of 'LVPI1801'.

Figure 3:
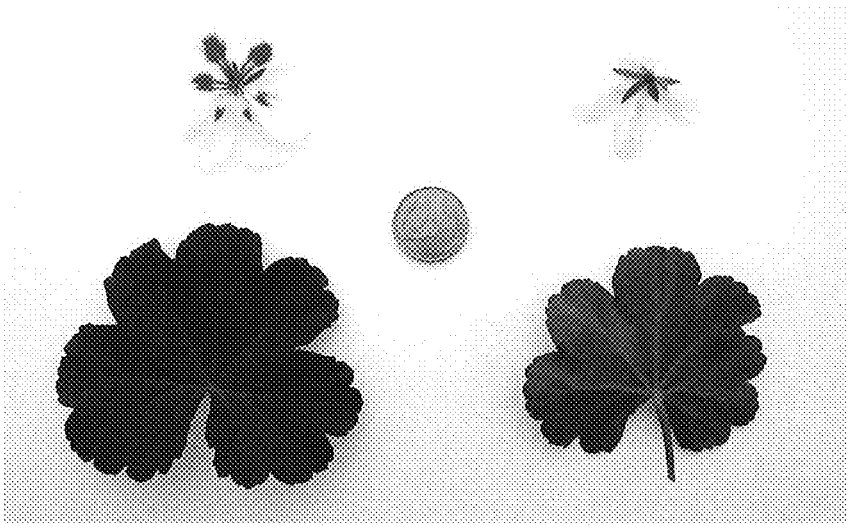

The photograph at the bottom of the second sheet (FIG. 3) are close-up views of the upper (left) and lower (right) surfaces of typical flowers and leaves of 'LVPI1801.'

DETAILED BOTANICAL DESCRIPTION

The aforementioned photograph and following observations, measurements and values describe plants grown in 12-cm containers during the autumn in a polyethylene-covered greenhouse in Merano, Italy and under cultural practices typical of commercial interspecific *Pelargonium* production. During the production of the plants, day temperatures ranged from 15° C. to 28° C. and night temperatures ranged from 10° C. to 18° C. Plants were twelve weeks old when the photographs and detailed description were taken. In the detailed description, color references are made to The Royal Horticultural Society Colour Chart, 2015 Edition, except where general terms of ordinary dictionary significance are used.

Botanical classification: *Pelargonium peltatum* X *Pelargonium zonale* 'LVPI1801'.

Parentage:

*Female, or seed, parent.*—*Pelargonium peltatum* 'Figradol Pink', trade name, Grand Idols Pink, disclosed in U.S. Plant Pat. No. 20,562.

*Male or pollen parent.*—*Pelargonium zonale* 'Gran Gala Dark with Magenta Eye', not patented.

Propagation:

*Type.*—By vegetative terminal cuttings.

*Time to initiate roots, summer.*—About 12 days at temperatures about 25° C.

*Time to initiate roots, winter.*—About 16 days at temperatures about 14° C.

*Time to produce a rooted young plant, summer.*—About three weeks at temperatures about 25° C.

*Time to produce a rooted young plant, winter.*—About four weeks at temperatures about 14° C.

*Root description.*—Fine, fibrous; typically creamy white in color, actual color of the roots is dependent on substrate composition, water quality, fertilizers, substrate temperature and age of roots.

*Rooting habit.*—Freely branching; medium density.

Plant description:

*Plant and growth habit.*—Compact, upright to broadly spreading plant habit; flattened globular in overall shape; densely foliated; moderately vigorous to vigorous growth habit and moderate growth rate; freely basal branching habit with about three primary lateral branches each with about three secondary lateral branches developing per plant; pinching is typically not required.

*Plant height, to top of foliar plane.*—About 14.7 cm.

*Plant height, to top of floral plane.*—About 25.4 cm.

*Plant width.*—About 30.7 cm.

*Lateral branches.*—Length: About 7.5 cm. Diameter: About 4.5 mm. Internode length: About 2.6 cm. Strength: Moderately strong. Aspect: About 30° to 80° from vertical. Texture and luster: Densely pubescent; slightly glossy. Color, developing: Close to 145B. Color, developed: Close to 144A, upper surface tinged with close to 177A and at the internodes, close to 144C.

Leaf description:

*Arrangement*.—Opposite and alternate; simple.

*Length*.—About 7.9 cm.

*Width*.—About 9.4 cm.

*Shape*.—Reniform.

*Apex*.—Rounded with a minute abruptly acute tip.

*Base*.—Hastate, lobes free and occasionally imbricate.

*Margin*.—Coarsely crenate; about five to nine lobes, each lobe with a minute abruptly acute tip; sinuses divergent and relatively shallow.

*Venation pattern*.—Palmate.

*Texture and luster, upper surface*.—Sparsely pubescent; velvety; slightly glossy.

*Texture and luster, lower surface*.—Moderately pubescent; velvety; slightly glossy.

*Color*.—Developing leaves, upper surface: Close to 137B. Developing leaves, lower surface: Close to 138B. Fully expanded leaves, upper surface: Slightly darker than a blend of close to NN137A and 147A; venation, close to 144A; no discernible zonation pattern. Fully expanded leaves, lower surface: Close to a blend of 137A and 147B; venation, close to 143B.

*Petioles*.—Length: About 6 cm. Diameter: About 2 mm. Strength: Moderately strong. Texture and luster, upper and lower surfaces: Densely pubescent; moderately glossy. Color, upper surface: Close to 143A. Color, lower surface: Close to a blend of 143B and 144A.

*Stipules*.—Quantity and arrangement: Two, opposite. Length: About 6 mm. Width: About 5 mm. Shape: Ovate to nearly deltoid. Apex: Acute. Base: Broadly cuneate. Texture, upper and lower surfaces: Moderately pubescent. Color, upper and lower surfaces: Close to 143A.

Flower description:

*Flower arrangement and flowering habit*.—Single-type rotate flowers arranged in hemispherical umbels arising from apical leaf axils; umbels displayed above the foliar plane on moderately strong peduncles; flowers face upright to outwardly depending on the position in the umbel; freely flowering habit with about 24 flowers developing per umbel and numerous umbels developing per plant during the flowering season.

*Fragrance*.—None detected.

*Flowering season*.—Early flowering habit; plants begin flowering about 30 days after planting; in the garden, flowering begins in the spring and continues until frost in the autumn.

*Flower longevity*.—Individual flowers last about one week on the plant; flowers persistent.

*Umbel height*.—About 7.2 cm.

*Umbel diameter*.—About 11.6 cm.

*Flower diameter*.—About 5.5 cm by 5.7 cm.

*Flower depth* (*height*).—About 1.7 cm.

*Flower buds*.—Length: About 1.5 cm. Diameter: About 5.5 mm. Shape: Elliptic. Texture and luster: Sparsely pubescent; slightly glossy. Color: Developing sepals, close to 143A; developing petals, close to 157D.

*Petals*.—Quantity per flower: Typically six, occasionally, seven, arranged in a single whorl. Length, upper petals: About 3.8 cm. Length, lower petals: About 3.3 cm. Width, all petals: About 2.1 cm. Shape, all petals: Broadly obovate. Apex, upper petals: Broadly retuse to broadly rounded. Apex, lower petals: Broadly rounded. Base, all petals: Acuminate. Margin, all petals: Entire; slightly undulate. Texture and luster, all petals, upper surface: Smooth, glabrous; velvety; matte. Texture and luster, all petals, lower surface: Smooth, glabrous; slightly velvety; matte. Color: When opening, upper petals, upper surface: Close to NN155D; conspicuous basal spot, close to a blend of N66B and 67B. When opening, lower petals, upper surface: Close to NN155D; small basal spot, close to a blend of N66B and 67B. When opening, upper petals, lower surface: Close to NN155C; basal venation, close to 63C. When opening, lower petals, lower surface: Close to NN155C; small basal spot, close to 63C. Fully opened, upper petals, upper surface: Close to NN155D; conspicuous basal spot, close to N66B; basal venation, close to 64B; color does not change with subsequent development. Fully opened, lower petals, upper surface: Close to NN155D; small basal spot, close to N66B; color does not change with subsequent development. Fully opened, upper petals, lower surface: Close to NN155D; basal spot, close to 69B; basal venation, close to 64B; color does not change with subsequent development. Fully opened, lower petals, lower surface: Close to NN155D; basal venation, close to 64D; color does not change with subsequent development.

*Petaloids*.—To date, petaloid development has not been observed on plants of the new interspecific *Pelargonium*.

*Sepals*.—Quantity per flower: Five arranged in a single whorl; one (upper) sepal slightly wider than the four lateral sepals. Length, all sepals: About 1.4 cm. Width, upper sepal: About 5 mm. Width, lateral sepals: About 3 mm. Shape, all sepals: Narrowly elliptic to narrowly oblong. Apex, all sepals: Apiculate. Base, all sepals: Cuneate. Margin, all sepals: Entire. Texture and luster, all sepals, upper surface: Smooth, glabrous; slightly glossy. Texture and luster, all sepals, lower surface: Sparsely pubescent; slightly glossy. Color: When opening, all sepals, upper surface: Close to 144A. When opening, upper sepal, lower surface: Close to 146B slightly tinged towards the apex with 181A. When opening, lateral sepals, lower surface: Close to 144A. Fully opened, upper sepal, upper surface: Close to 143A tinged towards the base with 181A. Fully opened, lateral sepals, upper surface: Close to 144A to 144B. Fully opened, upper sepal, lower surface: Close to a blend of 143B and 144A tinged with close to 178A. Fully opened, lateral sepals, lower surface: Close to a blend of 143B and 144A becoming tinged with close to 178B with subsequent development.

*Peduncles* (*umbel stems*).—Length: About 16.2 cm. Diameter: About 3 mm. Strength: Moderately strong; flexible. Aspect: About 30° from lateral branch axis. Texture and luster: Moderately pubescent; moderately glossy. Color: Close to darker than 143A; upper surface tinged with close to N200A.

*Pedicels* (*individual flower stems*).—Length: About 3.4 cm. Diameter: About 1.5 mm. Strength: Moderately strong; flexible. Aspect: Upright to about 90° from peduncle axis depending on position in the umbel. Texture and luster: Moderately pubescent; glossy. Color: Close to 152A; distally, strongly tinged with close to 200C to 200D; upper surface close to 177A to slightly darker than 177A.

*Floral bracts*.—Quantity and arrangement: About 24 at the top of the peduncle. Length: About 1 cm. Width: About 4 mm. Shape: Ovate to oblong. Apex: Apiculate. Base: Broadly cuneate. Texture, upper and lower surfaces: Moderately pubescent. Color, upper and lower surfaces: Close to 146A tinged with close to 166A.

*Reproductive organs*.—Androecium: Stamen quantity per flower: About ten. Filament length: About 9 mm. Filament color: Close to NN155C; distally, close to 68B. Anther size: About 1 mm by 2.5 mm. Anther shape: Oblong. Anther color: Close to 63A. Pollen amount: Abundant. Pollen color: Close to 172B. Gynoecium: Pistil quantity per flower: One. Pistil length: About 7 mm. Stigma diameter: About 4 mm. Stigma shape: Five-parted. Stigma color: Close to 64B. Style length: About 5 mm. Style color: Close to 145D. Ovary color: Close to N199B. Seeds and fruits: To date, seed and fruit development have not been observed on plants of the new interspecific *Pelargonium*.

Pathogen & pest resistance: To date, plants of the new interspecific *Pelargonium* have not been observed to be resistant to pathogens and pests common to interspecific *Pelargoniums*.

Garden performance & temperature tolerance: Plants of the new interspecific *Pelargonium* have been observed to have good garden performance, to tolerate temperatures ranging from about 5° C. to about 40° C. and to be suitable for USDA Hardiness Zones 10 to 13.

It is claimed:

1. A new and distinct interspecific *Pelargonium* plant named 'LVPI1801' as illustrated and described.

* * * * *